US010379038B2

(12) United States Patent
Stavis et al.

(10) Patent No.: US 10,379,038 B2
(45) Date of Patent: Aug. 13, 2019

(54) MEASURING A SIZE DISTRIBUTION OF NUCLEIC ACID MOLECULES IN A SAMPLE

(71) Applicant: Government of the United States of America, as represented by the Secretary of Commerce, Gaithersburg, MD (US)

(72) Inventors: Samuel Martin Stavis, North Potomac, MD (US); Craig Robert Copeland, Laurel, MD (US)

(73) Assignee: GOVERNMENT OF THE UNITED STATES OF AMERICA, AS REPRESENTED BY THE SECRETARY OF COMMERCE, Gaithersburg, MD (US)

( * ) Notice: Subject to any disclaimer, the term of this patent is extended or adjusted under 35 U.S.C. 154(b) by 0 days.

(21) Appl. No.: 15/715,761

(22) Filed: Sep. 26, 2017

(65) Prior Publication Data

US 2018/0106717 A1    Apr. 19, 2018

Related U.S. Application Data

(60) Provisional application No. 62/404,989, filed on Oct. 6, 2016.

(51) Int. Cl.
| *G01N 21/31* | (2006.01) |
| *G02B 21/36* | (2006.01) |
| *G01N 1/30* | (2006.01) |
| *G01N 21/64* | (2006.01) |
| *G01N 21/89* | (2006.01) |
| *C12Q 1/6825* | (2018.01) |
| *C12N 15/10* | (2006.01) |
| *G01N 21/88* | (2006.01) |
| *G01N 21/17* | (2006.01) |
| *G01N 21/55* | (2014.01) |
| *G01N 21/77* | (2006.01) |

(52) U.S. Cl.
CPC ....... *G01N 21/314* (2013.01); *C12N 15/1006* (2013.01); *C12Q 1/6825* (2013.01); *G01N 1/30* (2013.01); *G01N 21/6428* (2013.01); *G01N 21/6458* (2013.01); *G01N 21/8903* (2013.01); *G02B 21/361* (2013.01); *G02B 21/367* (2013.01); *G01N 2021/174* (2013.01); *G01N 2021/3129* (2013.01); *G01N 2021/3196* (2013.01); *G01N 2021/556* (2013.01); *G01N 2021/558* (2013.01); *G01N 2021/6419* (2013.01); *G01N 2021/6441* (2013.01); *G01N 2021/6491* (2013.01); *G01N 2021/7756* (2013.01); *G01N 2021/8883* (2013.01); *G01N 2201/1247* (2013.01)

(58) Field of Classification Search
CPC ... G01N 21/314; G02B 21/367; C12Q 1/6825
See application file for complete search history.

(56) References Cited

U.S. PATENT DOCUMENTS

| 5,356,776 | A | 10/1994 | Kambara et al. |
| 5,558,998 | A | 9/1996 | Hammond et al. |
| 5,720,598 | A | 2/1998 | de Chizzelle |
| 5,720,928 | A | 2/1998 | Schwartz |
| 5,977,344 | A | 11/1999 | Glazer et al. |
| 6,280,933 | B1 | 8/2001 | Glazer et al. |
| 6,309,386 | B1 | 10/2001 | Bek |
| 6,309,886 | B1 | 10/2001 | Ambrose et al. |
| 6,743,578 | B1 | 6/2004 | Castro |
| 6,927,065 | B2 | 8/2005 | Chan et al. |
| 8,423,294 | B2 | 4/2013 | Nadel et al. |
| 8,637,301 | B2 | 1/2014 | Wang et al. |
| 8,835,110 | B2 | 9/2014 | Wang et al. |
| 9,284,601 | B2 | 3/2016 | Wang et al. |
| 9,383,337 | B2 | 7/2016 | Quake et al. |
| 9,476,819 | B2 | 10/2016 | Wang et al. |
| 2005/0017191 | A1* | 1/2005 | Montagu ............ G01N 21/6452 250/393 |
| 2009/0238423 | A1* | 9/2009 | Rigler ............... G01N 35/00871 382/128 |
| 2011/0117127 | A1* | 5/2011 | Kost ................ G01N 27/44743 424/209.1 |

OTHER PUBLICATIONS

Shortreed et al, High-Throughput Single-Molecule DNA Screening Based on Electrophoresis, 2000, Anal. Chem., 72, 2879-2885 (Year: 2000).*
Kundukad et al, Effect of YOYO-1 on the mechanical properties of DNA, 2014, Soft Matter, 10, 9721-9728 (Year: 2014).*
Torchinsky et al , Sizing femtogram amounts of dsDNA by single-molecule counting, 2016, Nucleic Acids Research, 44, e17, pp. 1-6. (Year: 2016).*
Torchinsky et al , Sizing femtogram amounts of dsDNA by single-molecule counting, 2016, supplemental information, Nucleic Acids Research, 44, e17, pp. 1-14. (Year: 2016).*
Liu et al, Decoding Circulating Nucleic Acids in Human Serum Using Microfluidic Single Molecule Spectroscopy, 2010, JACS, 132, 5793-5798. (Year: 2010).*
Liu et al, Decoding Circulating Nucleic Acids in Human Serum Using Microfluidic Single Molecule Spectroscopy, 2010, JACS, 132, Supplemental information, pp. 1-6. (Year: 2010).*

(Continued)

*Primary Examiner* — Narayan K Bhat
(74) *Attorney, Agent, or Firm* — Office of Chief Counsel for National Institute of Standards and Technology

(57) ABSTRACT

A process for measuring a size distribution of a plurality of nucleic acid molecules, the process comprising: labeling the nucleic acid molecules with a fluorescent dye comprising a plurality of fluorescent dye molecules to form labeled nucleic acid molecules, such that a number of fluorescent dyes molecules attached to each nucleic acid molecule is reliably proportional to the number of base pairs in the nucleic acid molecule, the fluorescent dye molecules having a first florescence spectrum; producing, by the labeled nucleic acid molecules, the first florescence spectrum in response to irradiating the labeled nucleic acid molecules at the first wavelength; and detecting the first florescence spectrum to measure the size distribution of the plurality of nucleic acid molecules.

26 Claims, 9 Drawing Sheets

(56) References Cited

OTHER PUBLICATIONS

Che et al, Synthesis and characterization of chiral mesoporous silica, 2004, Nature, 429, 281-284 (Year: 2004).*
Grady et al, Disease progression in patients with single, large-scale mitochondrial DNA deletions, 2014, Brain, 137, 323-334. (Year: 2014).*
Data sheet, Invitrogen 10 bp DNA ladder, printed on Apr. 25, 2019, pp. 1-2. (Year: 2019).*
Huang, Z., et al., Large DNA fragment sizing by flow cytometry: Application to the characterization of P1 Artificial Chromosome (PAC) clones, Nucleic Acids Research, 1996; 4202-4209, 24(21).
Chou, H-P., et al, A microfabricated device for sizing and sorting DNA molecules, Proceedings of the National Academy of Sciences, 1999, 11-13, 96(1).
Foquet,M., et al., DNA Fragment Sizing by Single Molecule Detection in Submicrometer-Sized Closed Fluidic Channels, Analytical Chemistry, 2002, 1415-1422, 74(6).
Laib, S., et al., Sizing of single fluorescently stained DNA fragments by scanning microscopy, Nucleic Acids Research, 2003, e 138-e138, 31(22).
Reccius, CH., et al., Conformation, Length, and Speed Measurements of Electrodynamically Stretched DNA in Nanochannels, Biophys J, 2008, 273-286, 95(1).
Liu, KJ., et al., Decoding Circulating Nucleic Acids in Human Serum Using Microfluidic Single Molecule Spectroscopy, Journal of the American Chemical Society, 2010, 5793-5798, 132(16).
Pang, D., et al., Spatial distribution of radiation-induced double-strand breaks in plasmid DNA as resolved by atomic force microscopy, Radiat Res, 2005, 755-765, 164(6).
Mouliere, F., et al., Multi-marker analysis of circulating cell-free DNA toward personalized medicine for colorectal cancer, Molecular Oncology, 927-941, 8(5).
haab, BB., et al., Single-Molecule Detection of DNA Separations in Microfabricated Capillary Electrophoresis Chips Employing Focused Molecular Streams, Analytical Chemistry 1999, 5137-5145, 71(22).
Liu, KJ., et al., Single-Molecule Analysis Enables Free Solution Hydrodynamic Separation Using Yoctomole Levels of DNA, Journal of the American Chemical Society, 2011, 6898-6901, 133(18).
Zhu, Z. , et al., Simultaneously Sizing and Quantitating Zeptomole-Level DNA at High Throughput in Free Solution, Chemistry—A European Journal, 2014, 13945-13950, 20(43).
Friedrich, SM., et al., Single Molecule Hydrodynamic Separation Allows Sensitive and Quantitative Analysis of DNA Conformation and Binding Interactions in Free Solution, Journal of the American Chemical Society, 2016, 319-327, 138(1).

* cited by examiner

MEASURING A SIZE DISTRIBUTION OF NUCLEIC ACID MOLECULES IN A SAMPLE

CROSS REFERENCE TO RELATED APPLICATIONS

This application claims the benefit of U.S. Provisional Patent Application Ser. No. 62/404,989, filed Oct. 6, 2016, the disclosure of which is incorporated herein by reference in its entirety.

STATEMENT REGARDING FEDERALLY SPONSORED RESEARCH

This invention was made with United States Government support from the National Institute of Standards and Technology (NIST), an agency of the United States Department of Commerce. The Government has certain rights in the invention. Licensing inquiries may be directed to the Technology Partnerships Office, NIST, Gaithersburg, MD, 20899; voice (301)975-2573; email tpo@nist.gov; reference NIST Docket Number 16-044U51.

BRIEF DESCRIPTION

Disclosed is a process for measuring a size distribution of a plurality of nucleic acid molecules in a sample, the process comprising: labeling the nucleic acid molecules with a fluorescent dye comprising a plurality of fluorescent dye molecules to form labeled nucleic acid molecules, such that a number of fluorescent dyes molecules attached to each nucleic acid molecule is reliably proportional to the number of base pairs in the nucleic acid molecule, the fluorescent dye molecules having a first florescence spectrum; irradiating the sample at a first wavelength, the first wavelength exciting the labeled nucleic acid molecules in an absence of exciting the fluorescent nanoparticles; producing, by the labeled nucleic acid molecules, the first florescence spectrum in response to irradiating the multi-fluorescent composition at the first wavelength; and detecting the first florescence spectrum to measure the size distribution of the plurality of nucleic acid molecules.

BRIEF DESCRIPTION OF THE DRAWINGS

The following descriptions should not be considered limiting in any way. With reference to the accompanying drawings, like elements are numbered alike.

DETAILED DESCRIPTION

Figure 1:
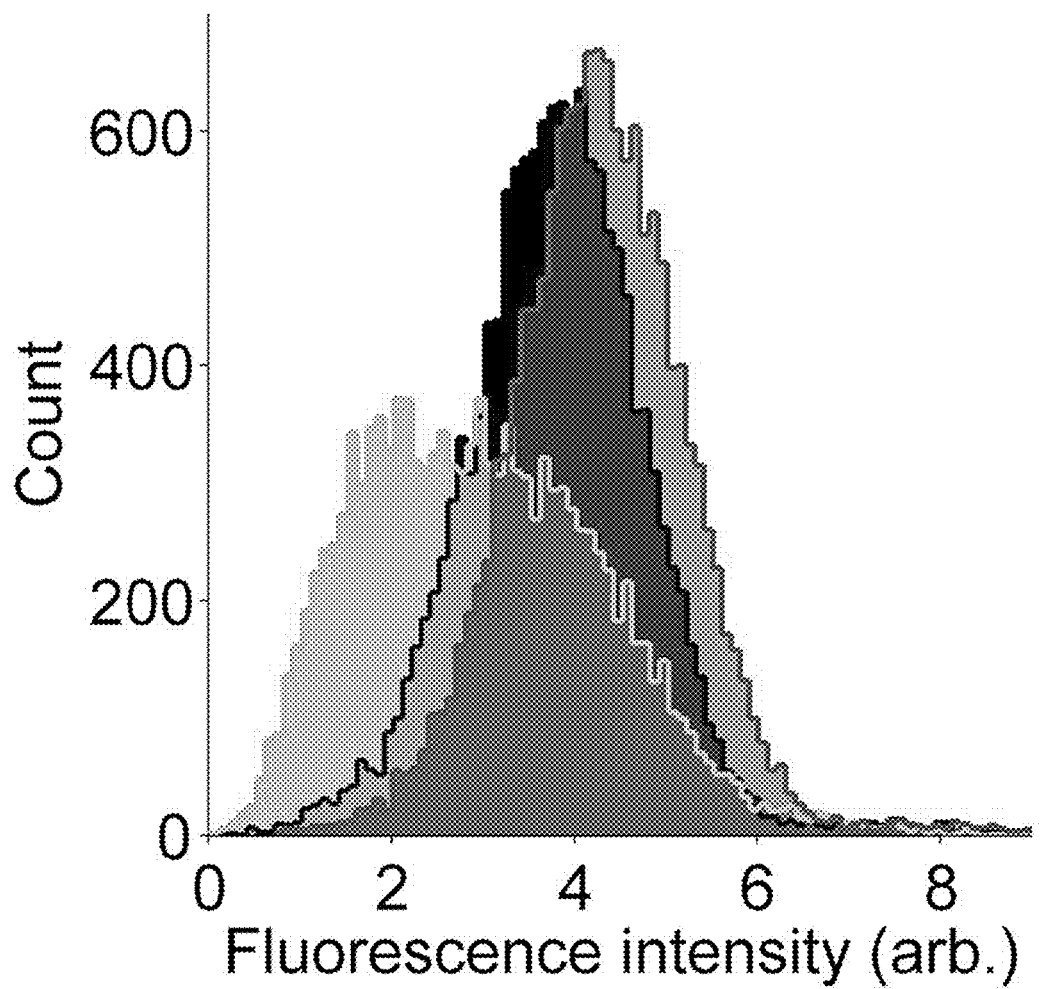
FIG. 1 shows a graph of count versus fluorescence intensity that illustrates an advantage of conditioning of a labeling reactor for reliably labeling DNA with intercalating fluorescent dye in proportion to the length of the DNA, wherein histograms showing the distribution of fluorescence intensity from a population of 500 bp DNA fragments labeled in (black) a large volume of solution in an unconditioned reactor, (green) a small volume of solution in an unconditioned reactor, and (blue) a small volume of solution in a conditioned reactor.

A detailed description of one or more embodiments is presented herein by way of exemplification and not limitation.

Advantageously and unexpectedly, it has been discovered that a process for measuring a size distribution of nucleic acid molecules provides advances in limit of detection, throughput, accuracy, precision, and repeatability. Moreover, the process determines a full distribution of DNA sizes in a sample. Additionally, the process quantitatively measures single DNA molecules with high precision.

Measuring a size of nucleic acid molecules is important in a wide variety of applications, ranging from criminal forensics to prenatal tests to liquid biopsies. The size distribution of cell-free DNA (cfDNA) molecules circulating in the bloodstream of patients can be a biomarker in medical applications, e.g., in cancer diagnostics where the size distribution of cfDNA can be an indicator of tumor burden, malignant progression, or treatment efficacy. Methods for quantitative, sensitive, rapid, and reliable measurement of the size distribution of nucleic acid molecules in a sample that can be readily adapted for routine clinical use are currently lacking, limiting such measurements as a clinical or treatment tool. For characterization of the size distribution of nucleic acid molecules in a sample, including all moments of the distribution and rare events, large quantities of single molecules should be measured. For application to clinical practice or treatment, the measurement method should include sufficient throughput to produce results in a reasonable amount of time. Polymerase chain reaction (PCR) is a commonly employed technique for a variety of applications in clinical diagnostics and research involving nucleic acids. For measurements of DNA size, PCR depends on targeting specific DNA sequences of known size for subsequent amplification and detection. While PCR is a powerful technique for many applications, because it only targets specific DNA sequences, PCR does not produce a true size distribution and does not size DNA. Electrophoretic techniques separate molecules by size and are generally not capable of detection and quantification at the level of single nucleic acid molecules, involving bulk measurements of nanograms of sample to estimate the size distribution. Atomic force microscopy (AFM) can measure the size of single nucleic acid molecules but is generally slow and involves specialized, expensive instrumentation. Single-molecule hydrodynamic separation is a promising technique for measuring the size of nucleic acid molecules and involves complex instrumentation with repeatability and reliability yet to be demonstrated.

Advantageously, the process herein provides high-throughput measurements of the size of single nucleic acid molecules and distributions of sizes of nucleic acid molecules in an absence of a complex measurement system with sample preparation, data acquisition, and analysis that produces reliable results. Sample preparation, imaging, and image-analysis provided by the process satisfy the need for quantitative, sensitive, rapid, reliable, and routine measurements of the size distribution of nucleic acid molecules in a sample.

According to an embodiment, a process for measuring a size distribution of a plurality of nucleic acid molecules includes: labeling the nucleic acid molecules with a fluorescent dye comprising a plurality of fluorescent dye molecules to form labeled nucleic acid molecules, such that a number of fluorescent dyes molecules attached to each nucleic acid molecule is proportional to the number of base pairs in the nucleic acid molecule, the fluorescent dye molecules having a first florescence spectrum; combining the labeled nucleic acid molecules with a plurality of fluorescent nanoparticles to form a multi-fluorescent composition, the fluorescent nanoparticles having a second fluorescent spectrum that is different than the first florescence spectrum; irradiating the multi-fluorescent composition at a second wavelength, the second wavelength exciting the fluorescent nanoparticles in an absence of exciting the labeled nucleic acid molecules; irradiating the multi-fluorescent composition at a first wavelength, the first wavelength exciting the labeled nucleic acid molecules in an absence of exciting the fluorescent nanoparticles; producing, by the labeled nucleic acid molecules, the first florescence spectrum in response to irradiating the multi-fluorescent composition at the first wavelength; and detecting the first florescence spectrum to measure the size distribution of the plurality of nucleic acid molecules. The process further can include measuring a concentration of the nucleic acid molecules.

In an embodiment, the process further includes disposing the nucleic acid molecules and the fluorescent dye molecules in a reactor to combine the nucleic acid molecules with the fluorescent dye molecules. Additionally, the process can include passivating the surface of the reactor prior to disposing the nucleic acid molecules and the fluorescent dye molecules in the reactor. Here, the surface can be passivated with respect to adsorption of the fluorescent dye molecules. The process can include incubating the nucleic acid molecules and the fluorescent dye molecules in the reactor; and reliably labeling the nucleic acid molecules with the fluorescent dye molecules. The fluorescent nanoparticles can include a negative surface charge such that disposing the multi-fluorescent composition on a substrate including a charge selective surface occurs prior to irradiating the multi-fluorescent composition at the first wavelength and the second wavelength, wherein the charge selective surface includes a surface density of positive charges. The process also can include selectively attracting and binding the labeled nucleic acid molecules and the fluorescent nanoparticles on the substrate through the positive charges of the charge selective surface of the substrate. In this manner, the process can include repelling free fluorescent dye molecules that are not attached to nucleic acid molecules in the labeled nucleic acid molecules, wherein the free fluorescent dye molecules are not adsorbed to the substrate. In an embodiment, the substrate includes a microscope cover glass.

It is contemplated that the process includes orienting and positioning an imaging surface of the substrate within a depth of field of an imaging system in an absence of perturbing the fluorescent dye molecules in the labeled nucleic acid molecules; adjusting a substrate holder to tip or tilt the imaging surface with respect to a focal plane of an objective lens of an imaging system; and positioning the imaging surface within the focal plane of the objective lens based on the second fluorescence spectrum of the fluorescent nanoparticles as positioning feedback.

According to an embodiment, the process includes simultaneously exciting a plurality of the fluorescent nanoparticles over a wide field with the second wavelength. The first wavelength and second wavelength can be independently provided from light-emitting diodes.

Detecting the first and second florescence spectra can be performed individually over a plurality of wide-field viewing areas. Also, the process can include moving the imaging surface relative to the imaging system to detect the first and second fluorescence spectra from the plurality of wide-field viewing areas. A size of single labeled nucleic acid molecules can be determined based on a quantitative calibration of the first fluorescence spectrum detected and nucleic acid molecule size in terms of a number of base pairs. The process can include correcting an image of the multi-fluorescent composition detected by the first fluorescence spectrum after irradiation with the first wavelength, wherein the image is corrected to account for a non-uniformity in an imaging sensor and a spatial distribution of first wavelength; measuring an intensity of the first fluorescence spectrum detected from single labeled nucleic acid molecules in the image; producing a calibration between the intensity of the first fluorescence spectrum and size of nucleic acid molecule with a reference sample comprising single sizes of reference nucleic acid molecules; modeling, with a selected function in a model, a dependence of a coefficient of variation of the intensity of the first fluorescence spectrum detected on nucleic acid molecule size; including, as an input to the model, a measured size of the labeled nucleic acid molecules; and determining, from the model, an uncertainty of the size of the single nucleic acid molecules of the labeled nucleic acid molecules. Beneficially, the nucleic acid molecules can have an unknown size, an unknown concentration, or a combination of comprising at least one of the foregoing unknowns.

In an embodiment, the process includes repeatable labeling of nucleic acid molecules with an intercalating fluorescent dye at a homogeneous ratio, e.g., of 1 fluorescent dye molecule to 4 base pairs (bp); dispersing the labeled nucleic acid molecules in a buffer composition that includes fluorescent nanoparticles as a microscopy reference to produce a multi-fluorescent composition that includes labeled nucleic acid molecules that include the fluorescent dye molecule attached to the nucleic acid molecule; disposing the multi-fluorescent composition on a substrate with a selected surface charge density; and imaging the labeled nucleic acid molecules via fluorescence from the labeled nucleic acid molecules.

Here, optical components and imaging hardware provide non-perturbative acquisition of fluorescence images of the labeled nucleic acid molecules for a reliable measurement. Image analysis quantifies the intensity of detected fluorescence or the fluorescence intensity of single nucleic acid molecules in each image and converts the measured intensity to size in terms of a number of base pairs. Moreover, determining the size of the nucleic acid molecules includes determining measurement uncertainty for quantitative results of the size. The nucleic acid can include DNA and the like, including cfDNA. The process achieves resolution and precision that exceed conventional methods using gel electrophoresis and other analytical modalities.

Labeling a nucleic acid molecule such as a DNA fragment with a fluorescent dye molecule that intercalates in the nucleic acid molecule produces a nucleic acid molecule-fluorescent dye molecule complex referred to herein as a labeled nucleic acid molecule. The labeled nucleic acid molecule contains a quantity of fluorescent dye molecules that is proportional to a length of the nucleic acid molecule. Under conditions for fluorescence, the intensity of fluorescence emitted by the labeled nucleic acid molecule or the number of fluorescence photons emitted is proportional to the number of fluorescent dye molecules in the labeled nucleic acid molecule and to the length of the nucleic acid molecule. The proportionality is provided because the process of labeling the nucleic acid molecules with the fluorescent dye molecule is repeatable.

The concentration of the nucleic acid molecules is determined because such concentration determines an amount of fluorescent dye molecules that achieves a selected ratio of fluorescent dye molecules to base pairs in the nucleic acid molecules. The concentration is determined with a fluorometer that is calibrated for measuring concentration of the nucleic acid molecules. In addition to the concentration of nucleic acid molecules in a sample, the amount of fluorescent dye molecules to label the nucleic acid molecules is controlled quantitatively. Undesirably, we have recognized that a positive charge of the fluorescent dye molecules can cause some fluorescent dye molecules to adsorb from an aqueous solution onto a surface of a reactor, e.g., a polymer or silica reactor. Such surfaces of the reactor can be negatively charged and that decreases the concentration of fluorescent dye molecules in a labeling solution, e.g., the buffer composition. For relatively large sample volumes on the order of milliliters, the ratio of the surface area of the reactor to the volume of the labeling solution may be sufficiently low to achieve labeling that maintains the desired ratio of fluorescent dye molecules to base pairs of the nucleic acid molecules. In contrast, for relatively small sample volumes on the order of tens of microliters, the ratio of surface area to volume is high enough that this loss of fluorescent dye molecules reduces the ratio of fluorescent dye molecules to base pairs of the nucleic acid molecules in the labeling solution and results in labeling that does not maintain the desired ratio of dye molecules to DNA base pairs.

In particular, the availability of clinical nucleic acid samples may involve small volumes of sample, the effects of which must be accounted for in a reliable measurement. The process overcomes this problem and achieves reliable labeling of small volumes of sample containing nucleic acid molecules by conditioning of the reactor for labeling by incubation with an aqueous solution of fluorescent dye molecules prior to the addition of nucleic acid molecules. Conditioning the reactor passivates exposed surfaces such as walls of the reactor and inhibits adsorption of fluorescent dye molecules out of the labeling solution in subsequent reactions.

The nucleic acid molecules may be single-stranded or double-stranded DNA or RNA. Exemplary nucleic acid molecules include double-stranded DNA molecules. In an embodiment, the nucleic acid molecules include cell-free DNA from the blood of a cancer patient. A size of the nucleic acid molecules can be from 10 base pairs (bp) to many thousands of base pairs. A concentration of the nucleic acid molecules can be as low as 0.01 ng/µl, depending on the method used to make the concentration measurement, and has no upper limit.

Fluorescent dye molecules selectively bind to the nucleic acid molecules in quantities proportional to the size of the nucleic acid molecules. Exemplary fluorescent dye molecules include intercalating dyes such as monomeric and dimeric cyanine nucleic acid stains. In an embodiment, the fluorescent dye molecules include YOYO-1 iodide.

The labeled nucleic acid molecules contain a number of bound dye molecules that is proportional to their length. Exemplary labeled nucleic acid molecules include DNA or RNA with 1 intercalating dye molecule bound per 4 or 5 base pairs. In an embodiment, the labeled nucleic acid molecules include cell-free DNA molecules with 1 YOYO-1 dye molecule per 4 base pairs.

The number of fluorescent dyes molecules attached to each nucleic acid molecule in the labeled nucleic acid molecules can be from 1 to thousands, specifically from 1 total to 1 dye molecule per 4 base pairs for dimeric cyanine nucleic acid stains.

Fiducial markers are optically detectable objects with a size on the scale of nanometers to micrometers. These objects adsorb, bind, or are otherwise attached to the imaging substrate to serve as fiducials for positioning the imaging surface. The spectrum for excitation and detection, through mechanisms such as fluorescence or scattering, is selectable to be distinct from the fluorescent dye molecules that label the labeled nucleic acid molecules. Exemplary fiducial markers include polymeric nanoparticles loaded with fluorescent dye, plasmonic nanoparticle scatterers, fabricated structures that scatter or absorb incident light. In an embodiment, the fiducial particles include polystyrene nanoparticles 40 nm in diameter and loaded with a fluorescent dye with a nominal excitation wavelength of 660 nm and a nominal emission wavelength of 680 nm. The fiducial particles can include a negative surface charge due to surface functionalization, such as attachment of carboxyl groups.

The fluorescent dye molecules have a first florescence spectrum that is different than the second spectrum of the fiducial particles. The first fluorescence spectrum can include wavelengths from 300 nm to 900 nm, specifically having excitation and emission spectra that are restricted to subsets of this range. The second spectrum can include wavelengths from 300 nm to 900 nm, specifically including wavelengths that are distinct from the first fluorescence spectrum.

With regard to the first fluorescence spectrum, the first wavelength can be from 300 nm to 900 nm, specifically over a range of approximately 100 nm centered around the nominal excitation wavelength of the fluorescent dye molecules. With regard to the second spectrum, the second wavelength can be from 300 nm to 900 nm, specifically over a range of approximately 100 nm centered around the nominal excitation wavelength of the fiducial particles, which is also distinct from the first fluorescence spectrum.

The reactor is a vessel suitable for holding liquids, particularly in small volumes, and is sealable to prevent evaporation. Exemplary reactors include polymer or silica test tubes, microcentrifuge tubes, and beakers. In an embodiment, the reactor includes a polymer microcentrifuge tube.

The substrate on which the sample containing the nucleic acids and the fiducial particles are disposed is flat, rigid, and provides a surface that contains the sample and allows imaging. Exemplary substrates include microscope slides and microscope cover glass. In an embodiment, the substrate includes microscope cover glass. The substrate can include a surface density of positive charges from functionalization by attaching or depositing a layer of positively charged polymer, such as poly-1-lysine or poly-d-lysine, or addition of amine groups to the substrate surface.

The imaging system can include an optical microscope equipped with light-emitting diodes for illumination with the first and second wavelengths, filter sets for illumination with and detection of the first fluorescence spectrum and the second spectrum, an imaging sensor for detecting the first and second spectra. In an embodiment, the imaging sensor is a complementary metal-oxide-semiconductor (CMOS) sensor. In an embodiment, the microscope includes of a motorized sample holder for rapidly positioning the substrate in 3 dimensions.

FIG. 1 shows the results of labeling 500 bp nucleic acid molecules under three conditions. The black distribution shows the result of reliable labeling from a large volume of solution in an unconditioned reactor. The green distribution shows the result of unreliable labeling from a small volume of solution in an unconditioned reactor, and the blue distribution shows the result of reliable labeling from a small volume of solution in a conditioned reactor. Conditioning the reactor leads to reliable labeling even for small volumes of sample. The shift between the black and blue distributions is due to sampling variability.

Embodiments provide wide-field measurements that are sensitive to nucleic acid molecules that are smaller than 50 base pairs. Sensitivity of detection for imaging single DNA molecules is primarily dependent on detecting a sufficient fluorescence intensity or number of photons from labeled DNA molecules to distinguish the DNA molecule from the background in the image. In an embodiment, an imaging system maximizes a sensitivity for measuring fluorescence for single-molecule detection of the nucleic acid molecule having, e.g., 20 base pairs. For fluorescence excitation, light emitting diodes (LEDs) provide illumination over a wide field with sufficient power to resolve approximately 20 bp fragments. The imaging system includes a fluorescence filter set and a CMOS imaging sensor that has a high quantum efficiency for maximizing the collection of photons emitted by the fluorescent dye molecule and reducing the effects of shot noise. In addition to shot noise, florescent dye molecules in the sample solution that are not bound to nucleic acid molecules can degrade a detection limit. Free fluorescent dye molecules in solution exhibit relatively low fluorescence when not intercalated into a nucleic acid molecule and bright fluorescence upon binding and intercalation with the nucleic acid molecule. The mechanism that causes this transition is the confinement of the dye molecule that results from intercalation. A similar confinement resulting in bright fluorescence can occur when a fluorescent dye molecule is bound to other entities such as a silica substrate. It is contemplated that the substrate includes a surface functionalization that has a positive surface charge for non-specific binding of negatively charged DNA molecules. Free fluorescent dye molecules can be positively charged and repelled from the functionalized surface of the substrate. When a region of the substrate contains unfunctionalized silica, fluorescent dye molecules unbound to nuclear gas molecules can adsorb to the surface. The fluorescence emitted from such fluorescent dye molecules can be bright enough to be indistinguishable from labeled DNA molecules of less than 20 bp. Accordingly, the imaging substrate used avoids binding of free fluorescent dye molecules.

The process for determining the size also includes non-perturbative imaging. Perturbative imaging degrades the labeled nucleic acid molecules by exposing the molecules to exciting radiation prior to the intended irradiation with the first wavelength. Degradation can include photobleaching of the fluorescent dye molecules and damage of the nucleic acid molecule, which may introduce errors in the proportionality of the size of a nucleic acid molecule with the number of bound dye molecules and the intensity of the first fluorescence spectrum. Beneficially, non-perturbative imaging ensures that the labeled nucleic acid molecules are only subject to exciting radiation during the intended irradiation with the first wavelength, such that the proportionality of the size of the nucleic acid molecules with the number of bound fluorescent dye molecules and the intensity of the first fluorescence spectrum remains accurate.

Imaging a fluorescence spectrum from the labeled nucleic acid molecules includes positioning the labeled nucleic acid molecules within the focal plane of the imaging system. Conventionally, positioning brings the sample into focus using a signal from the sample as feedback that in the case of single-molecule fluorescence can cause photobleaching and degradation of the sample. The degree of photobleaching can depend on a duration of illumination and can vary based on a time to position the sample. This uncontrolled degradation inhibits repeatable measurements over multiple images. The process overcomes these limitations and provides quantitative and repeatable measurements of fluorescence intensity from a plurality of images that are not perturbative to the labeled nucleic acid molecules. According to an embodiment, a method for positioning the sample of labeled nucleic acid molecules within the focal plane of the imaging system occurs in the absence of exciting the intercalated fluorescent dye molecules in the labeled nucleic acid molecules. The labeled nucleic acid molecules are disposed in a solution containing fluorescent nanoparticles that are fiducials for positioning the labeled nucleic acid molecules within the focal plane of the imaging system. The absorption and emission spectra of the fluorescent nanoparticles are distinct from the first fluorescence spectrum of the intercalated fluorescent dye molecules in the labeled nucleic acid molecules. Accordingly, illumination for positioning the labeled nucleic acid molecules does not photo bleach or otherwise perturb the labeled nucleic acid molecules.

Figure 2:
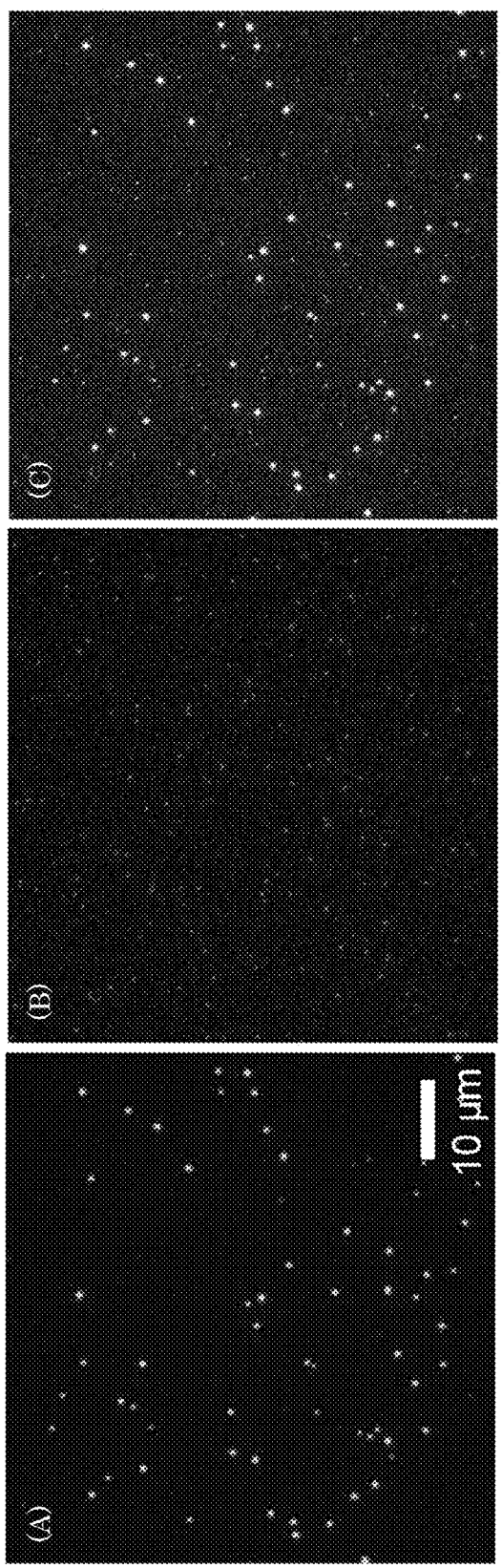
FIG. 2 shows images of fluorescently labeled DNA and fluorescent nanoparticles for automated focus without perturbation and includes fluorescence micrographs showing (a) a red nanoparticle channel, (b) a green DNA channel, and (c) a composite of the two channels. The signal from the nanoparticle channel enables positioning of the sample in the focal plane of the imaging system without exposing the DNA channel to degrading illumination.
Figure 3:
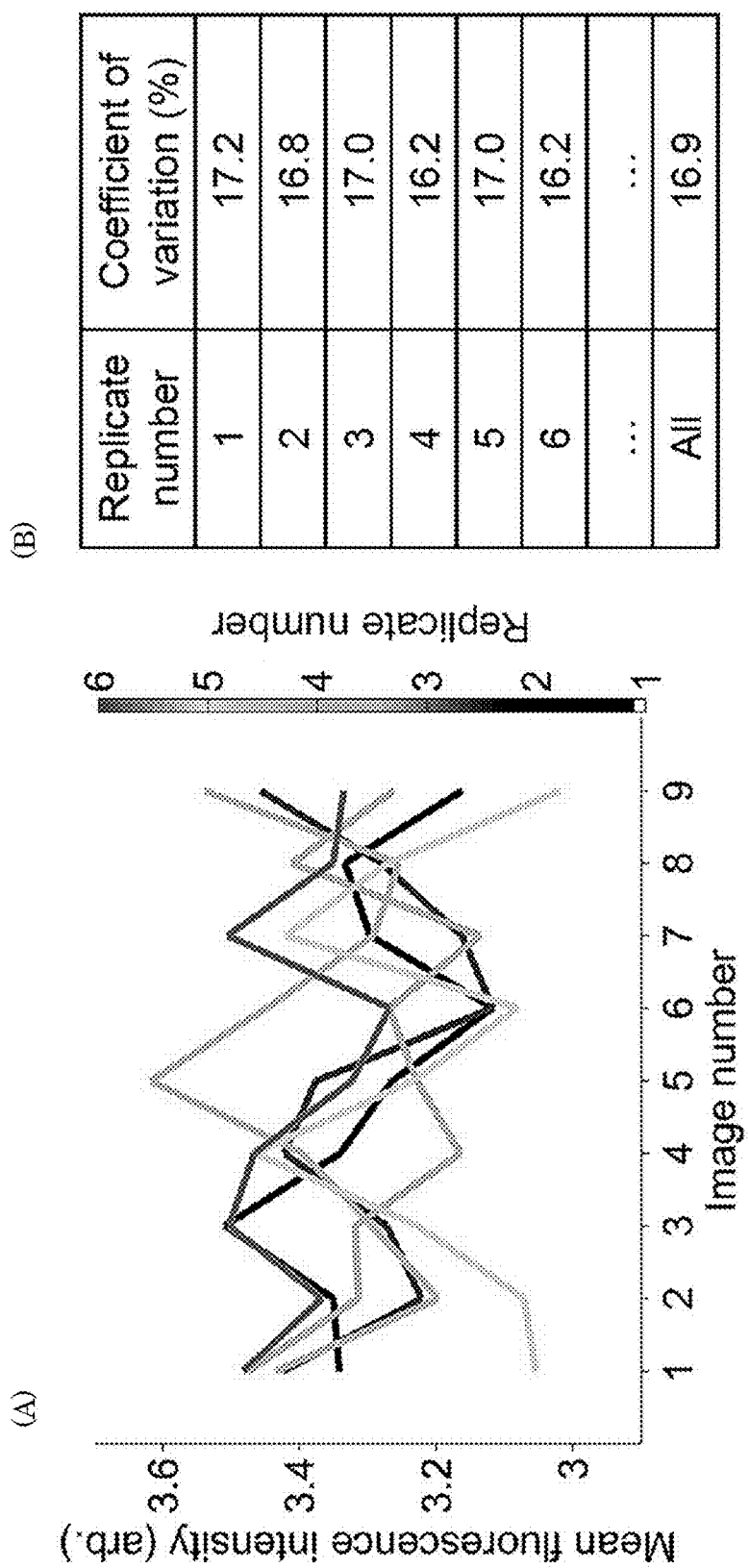
FIG. 3 shows (a) a graph of mean values of fluorescence intensity for 6 replicates of 9 images each from a single sample, and panel (b) shows coefficients of variation for the 6 replicates in panel (a) and the aggregate of all 6 replicates.

It is contemplated that a difference between the out-of-plane positions of a center of mass of the labeled nucleic acid molecules and that of the fluorescent nanoparticles is much smaller than a depth of field of an objective lens with a high numerical aperture and does not degrade the image of the labeled nucleic acid molecules. This process for non-perturbative positioning of the sample provides optimal focus over a wide field and repeatable results from multiple images. FIG. 2 shows images of a region of interest in both a red fluorescence channel for fluorescent nanoparticles that indicated the optimal position of the labeled nucleic acid molecules and a green fluorescence channel for labeled nucleic acid molecules. Moreover, FIG. 3a shows a plot of mean values of fluorescence intensity for 6 replicates of 9 images each from a single sample, and FIG. 3b lists coefficients of variation for each replicate in FIG. 3a and aggregate of all 6 replicates. Consistency of these values indicates that there is no significant variation between replicate measurements of the same sample.

Embodiments herein can include automated data acquisition and analysis. Using the fluorescence signal from the red fluorescence channel of fluorescent nanoparticles, a software algorithm automatically moves the objective lens to bring the surface of the substrate into the focal plane of the imaging system, maximizing the intensity of the signal in the red fluorescence channel, prior to acquiring an image in the green fluorescence channel of the labeled nucleic acid molecules. A motorized sample holder moves the substrate in the plane to allow for the acquisition of multiple images of a single sample of the labeled nucleic acid molecules with high throughput. The multiple regions of the sample of the labeled nucleic acid molecules that are imaged are selectively spaced to maximize throughput while ensuring that illumination for each acquisition does not perturb adjacent regions of the sample. The throughput of the process additionally benefits from the large field of view of the CMOS imaging sensor. For wide field imaging and elimination of errors caused by molecules that are out of focus, the substrate on which the labeled nucleic acid molecules are disposed can be positioned to be level with respect to a focal plane of the imaging system. For this, the imaging system includes a sample holder that adjusts a tip and tilt of the substrate. The high throughput of the process provides measurement of size through imaging of tens of thousands of labeled nucleic acid molecules during a period, e.g., of minutes and determines measured size distributions with a small coefficient of variation.

Figure 4:
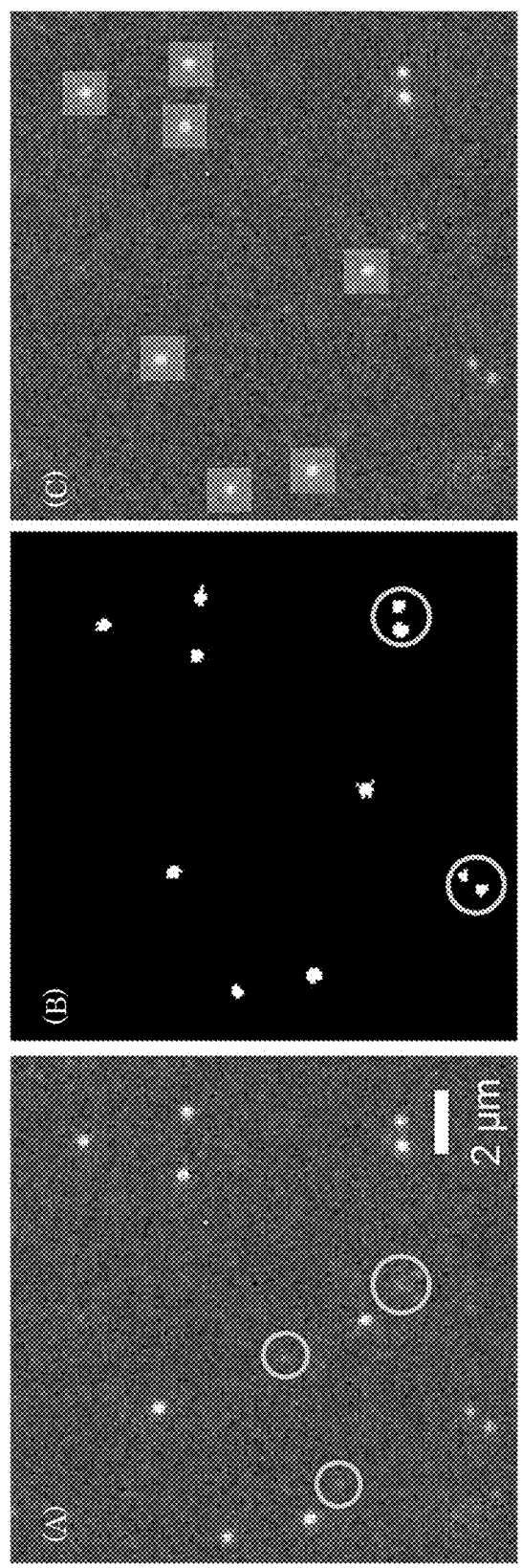
FIG. 4 shows, in panel (a), a fluorescence micrograph of single DNA molecules in which the red circles indicate features removed by intensity thresholding; panel (b) shows a binary micrograph produced by intensity thresholding in which red circles indicate molecules that are too close together for accurate integration of fluorescence intensity, and panel (c) shows a fluorescence micrograph of a subset of DNA molecules from (a) that are suitable for analysis in which green squares indicate the analyzed molecules and the size of the region of interest for integration of fluorescence intensity.

The process also includes analysis of measurement uncertainty for the conversion of quantified measurements of fluorescence intensity to size of nucleic acid molecules with a quantitative uncertainty. Automated image analysis software applies to each pixel in an image a scale factor that accounts for nonuniformities of the camera sensor and the illumination profile of the LED used for fluorescence excitation in the fluorescence channel of the labeled nucleic acid molecules. The software then locates and quantifies the fluorescence intensity of each labeled nucleic acid molecule in the image. Here, an automated intensity threshold distinguishes signal from background to produce a binary image. An area threshold operating on the binary image distinguishes single labeled nucleic acid molecules from large debris, aggregates, and background features. Labeled nucleic acid molecules that are too close to one another or to an edge of the image for an accurate measurement of fluorescence intensity can be ignored in subsequent analysis. FIG. 4 shows results from the analysis.

Figure 5:
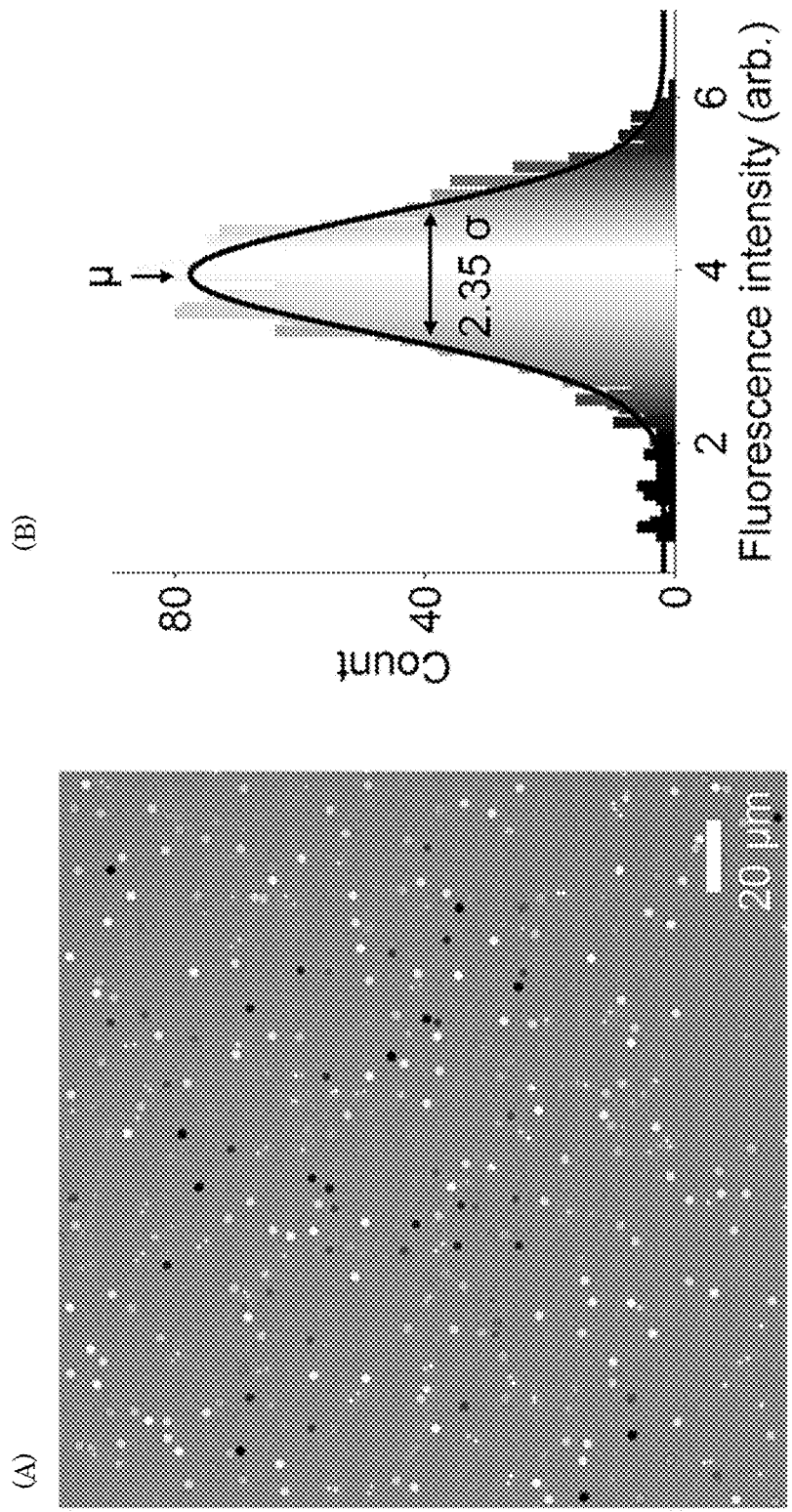
FIG. 5 shows measurements of a pure population of a single known fragment size result in a Gaussian distribution of fluorescence intensities in which panel (a) is an analyzed fluorescence micrograph showing 50 base pair (bp) DNA fragments, wherein colored circles indicate the measured fluorescence intensity of the underlying DNA molecule on the color scale that (b) shows. (b) Histogram of measured fluorescence intensities for the DNA molecules that (a) shows. The mean value of the distribution corresponds to the value of fluorescence intensity associated with the known size of the population, and the standard deviation is the uncertainty of this value.

The centroid of each labeled nucleic acid molecule in the binary image determines the position of an associated region of interest around each labeled nucleic acid molecule. Such regions are indicated by green boxes in FIG. 4c. Integration of the values of all pixels in the region of interest determines a raw intensity value for the labeled nucleic acid molecule. The contribution from background fluorescence is removed from the raw intensity value by subtracting from it the average background per pixel multiplied by the total number of pixels in the region of interest. FIG. 5a shows an image containing 50 bp labeled nucleic acid molecules with colored circles overlaid onto the analyzed labeled nucleic acid molecule. The color of each circle corresponds to the distribution of fluorescence intensity that FIG. 5b shows.

Figure 6:
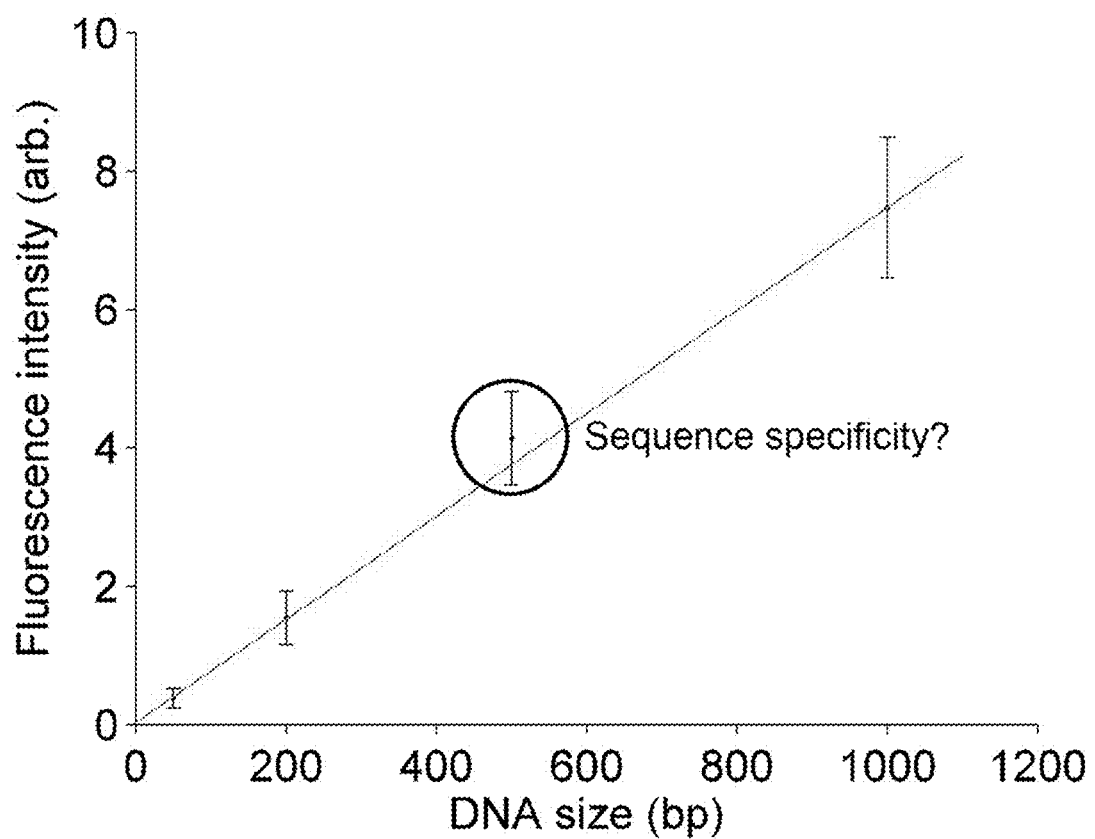
FIG. 6 shows a graph of fluorescence intensity versus DNA size for measured fluorescence intensity scales linearly with DNA size for populations of 50 bp, 200 bp, 500 bp, and 1000 bp DNA fragments. A linear fit models the relationship between fluorescence intensity and DNA size. Vertical bars are 1 standard deviation.
Figure 7:
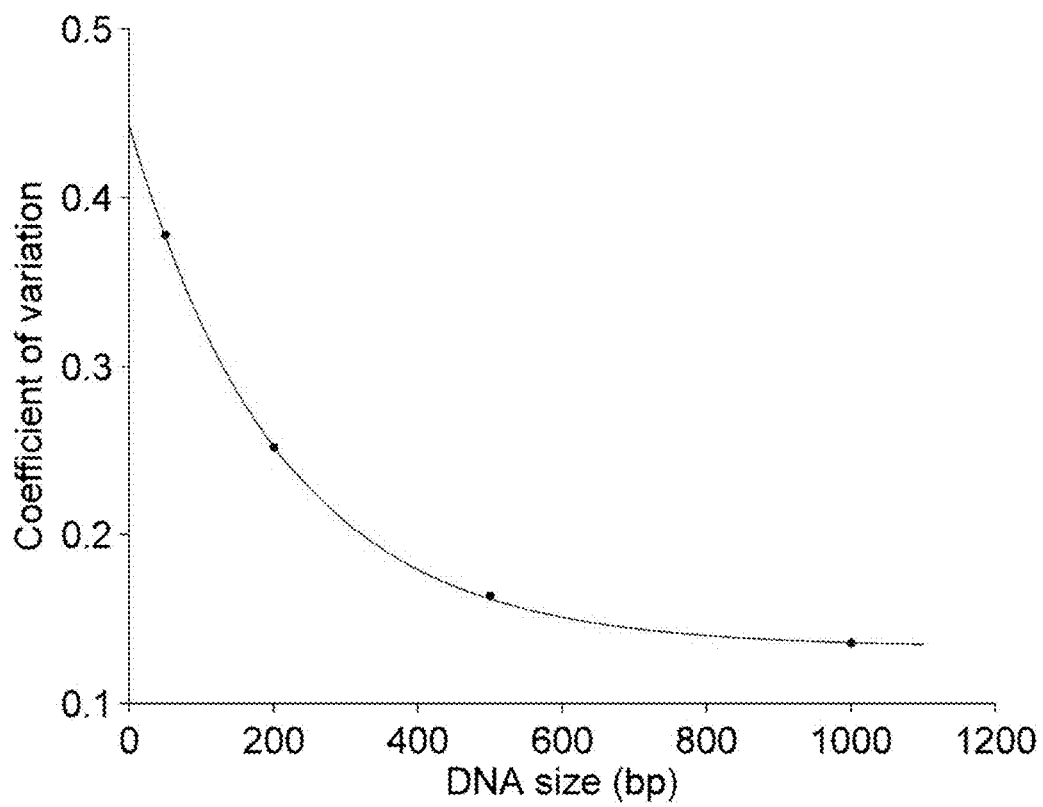
FIG. 7 shows a graph of coefficient of variation versus DNA size in which measured fluorescence intensity scales exponentially with DNA size for populations of 50 bp, 200 bp, 500 bp, and 1000 bp DNA fragments. An exponential fit models the relationship between the coefficient of variation and DNA size, which determines the uncertainties of measurements of DNA fragments of unknown size.

Multiple samples each containing labeled nucleic acid molecules of a single known size are used as a calibration standard for the determination of size of the labeled nucleic acid molecules from fluorescence intensity. FIG. 5b shows the Gaussian distribution of fluorescence intensities from measurements of one such sample of 50 bp labeled nucleic acid molecules. The average $\mu$ of the distribution is the value of fluorescence intensity associated with a length of 50 bp, and the standard deviation $\sigma$ of the distribution is the uncertainty of this value. FIG. 6 shows a plot of $\mu$ as a function of fragment size for samples of 50 bp, 200 bp, 500 bp, and 1000 bp labeled nucleic acid molecules, and a fit to a linear model. This empirical model converts fluorescence intensity to size of labeled nucleic acid molecules in samples with unknown size distributions of the labeled nucleic acid molecules. FIG. 7 shows a plot of $\sigma/\mu$ as a function of fragment size for the same samples, and a fit to an exponential model. This second empirical model determines the uncertainties of measurements of samples with unknown size distributions of the labeled nucleic acid molecules.

Figure 8:
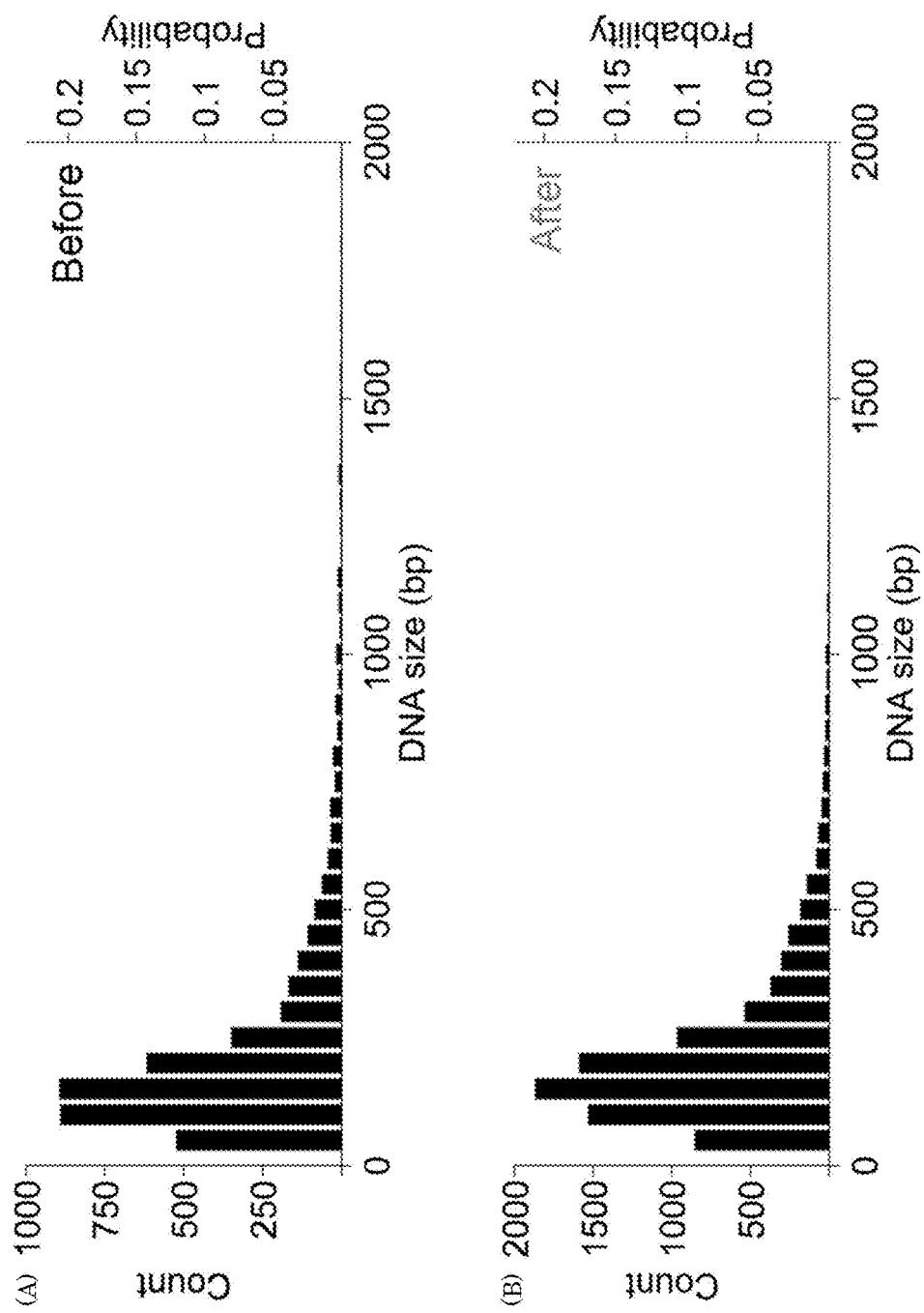
FIG. 8 shows graphs of count versus DNA size for blood of a liver cancer patient in which the histograms show measured size distributions (a) before and (b) after treatment by transarterial radioembolization.
Figure 9:
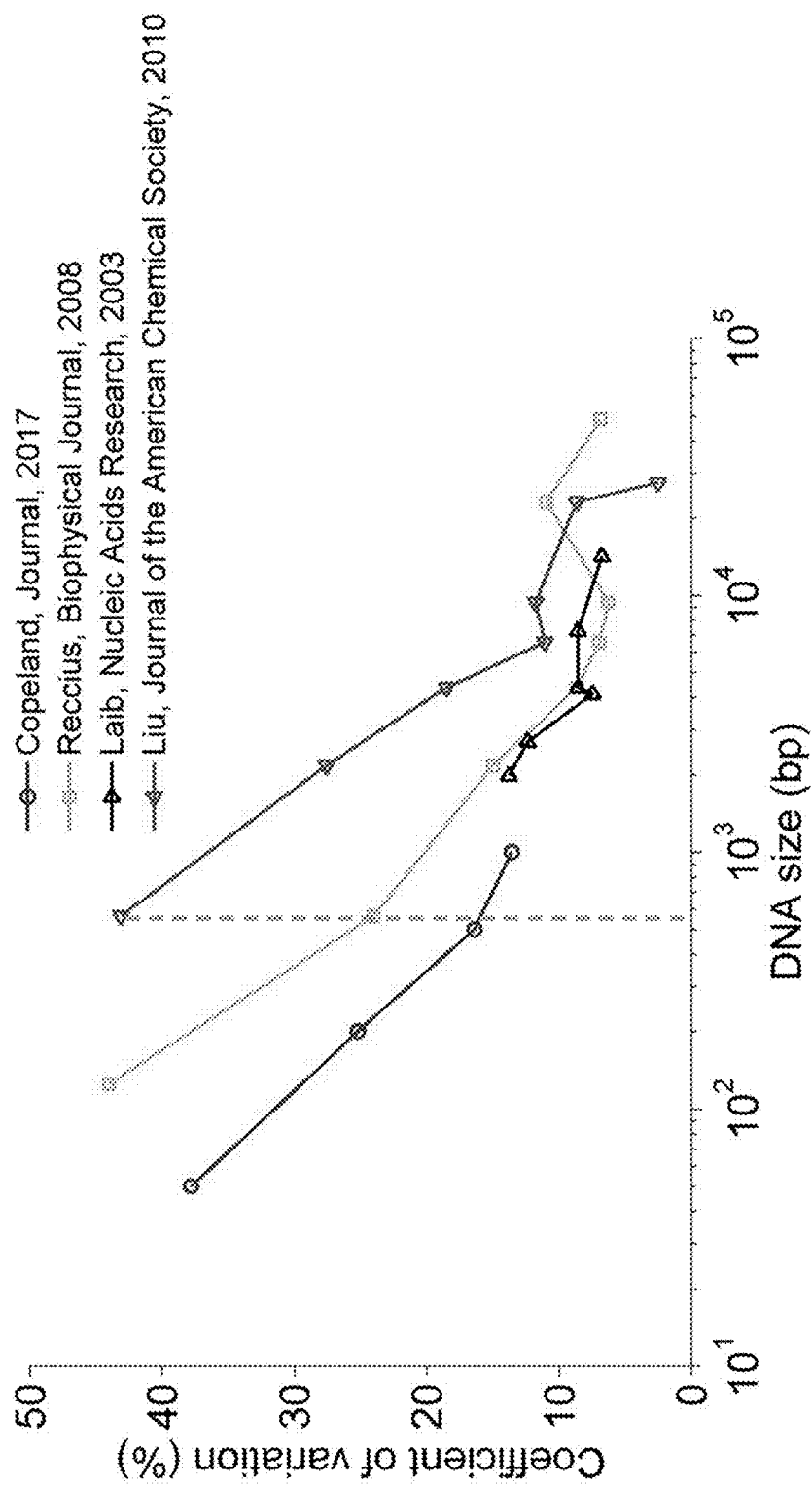
FIG. 9 shows a graph of coefficient of variation versus DNA size for performance comparison with DNA fragments sizing as measured by fluorescence collection.

FIG. 8 shows the measured distributions of size of labeled nucleic acid molecules in samples of cfDNA from a liver cancer patient before and after treatment by transarterial radioembolization.

In an embodiment, multicolor fluorescence imaging provides multiplexing of size measurements of labeled nucleic acid molecules with the detection of additional fluorescent targets. Fluorescent labeling of particular binding proteins or specific mutations provides correlated measurements with size of labeled nucleic acid molecules at the level of single labeled nucleic acid molecules such as single DNA fragments.

Advantageously, the process provides high-throughput measurements of the size of single nucleic acid molecules and distributions of sizes of nucleic acid molecules in an absence of a complex measurement system with sample preparation, data acquisition, and analysis that produces reliable results. Sample preparation, imaging, and image analysis provided by the process satisfy the need for quantitative, sensitive, rapid, reliable, and routine measurements of the size distribution of nucleic acid molecules in a sample.

Embodiments of the subject matter and the operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions, encoded on a computer storage medium for execution by, or to control the operation of, data processing apparatus. Alternatively, or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more computers executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, can be based on general or special purpose microprocessors or both, workstations, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic; magneto-optical disks, optical disks, USB drives, and so on. However, a computer need not have such devices. Moreover, a computer can be embedded in another device, e.g., a mobile telephone, a personal digital assistant (PDA), a microwave oven, mobile audio or video player, a game console, a Global Positioning System (GPS) receiver, or a portable storage device (e.g., a universal serial bus (USB) flash drive), to name just a few. Devices suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The central processing unit and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks). Such interconnects may involve electrical cabling, fiber optics, or be wireless connections.

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. A process for measuring a size distribution of a plurality of nucleic acid molecules, the process comprising:
    labeling the nucleic acid molecules with a fluorescent dye comprising a plurality of fluorescent dye molecules to form labeled nucleic acid molecules, such that a number of fluorescent dyes molecules attached to each nucleic acid molecule is reliably proportional to the number of base pairs in the nucleic acid molecule for nucleic acid molecules consisting of 10 base pairs to 50 base pairs, and the fluorescent dye molecules having a first florescence spectrum;
    producing, by the labeled nucleic acid molecules, the first florescence spectrum in response to irradiating the labeled nucleic acid molecules at the first wavelength; and
    detecting the first florescence spectrum to measure the size distribution of the plurality of nucleic acid molecules for nucleic acid molecules consisting of 10 base pairs to 50 base pairs; and
    determining a size of single nucleic acid molecules in the labeled nucleic acid molecules, based on a quantitative calibration of the first fluorescence spectrum detected and nucleic acid molecule size in terms of a number of base pairs.

2. The process of claim 1, further comprising measuring a concentration of the nucleic acid molecules.

3. The process of claim 2, further comprising disposing the nucleic acid molecules and an amount of the fluorescent dye in a reactor to combine the nucleic acid molecules with the fluorescent dye molecules at a specific ratio of nucleic acids to dye molecules, the amount of fluorescent dye based on the concentration of the nucleic acid molecules.

4. The process of claim 3, further comprising passivating a surface of the reactor prior to disposing the nucleic acid molecules and the fluorescent dye molecules in the reactor.

5. The process of claim 4, wherein the surface is passivated with respect to adsorption of the fluorescent dye molecules.

6. The process of claim 5, further comprising incubating the nucleic acid molecules and the fluorescent dye molecules in the reactor; and
reliably labeling the nucleic acid molecules with the fluorescent dye molecules in proportion to their length.

7. The process of claim 6, wherein the fluorescent dye molecules comprise a positive charge and the labeled nucleic acid molecules comprise a net negative charge.

8. The process of claim 7, further comprising disposing the labeled nucleic acid molecules on a substrate comprising a charge selective surface, such that the disposing occurs prior to irradiating the labeled nucleic acid molecules at the first wavelength.

9. The process of claim 8, wherein the charge selective surface comprises a surface density of positive charges.

10. The process of claim 9, further comprising selectively attracting and binding the labeled nucleic acid molecules on the substrate through the positive charges of the charge selective surface of the substrate.

11. The process of claim 10, further comprising selectively repelling free fluorescent dye molecules that are not attached to nucleic acid molecules in the labeled nucleic acid molecules,
wherein the free fluorescent dye molecules are not absorbed to the substrate.

12. The process of claim 11, wherein the substrate comprises a cover glass.

13. The process of claim 12, further comprising orienting and positioning an imaging surface of the substrate through a depth of field of an imaging system in an absence of perturbing the fluorescent dye molecules in the labeled nucleic acid molecules.

14. The process of claim 13, further comprising disposing onto the imaging substrate a plurality of fiducial markers, the fiducial markers having a second wavelength and spectrum for optical detection that is different than the first wavelength and first florescence spectrum.

15. The process of claim 14, further comprising:
adjusting a substrate holder to orient the imaging surface with respect to a focal plane of an objective lens of an imaging system; and
positioning the imaging surface through the focal plane of the objective lens based on the second spectrum of the fiducial markers as positioning feedback.

16. The process of claim 15, further comprising irradiating the substrate at the first wavelength, prior to disposing the sample containing the labeled nucleic acid molecules, and collecting a background spectrum corresponding to the first fluorescence spectrum.

17. The process of claim 16, further comprising simultaneously exciting a plurality of the fiducial markers over a wide field with the second wavelength.

18. The process of claim 17, further comprising providing the second wavelength from a light-emitting diode; and
providing the first wavelength from a light-emitting diode.

19. The process of claim 18, wherein detecting the first florescence spectrum is performed individually over a plurality of wide-field viewing areas through imaging.

20. The process of claim 19, wherein the imaging sensor is a complimentary metal-oxide-semiconductor (CMOS) sensor.

21. The process of claim 20, further comprising moving the imaging surface relative to the objective lens to detect the first fluorescence spectrum from the plurality of wide-field viewing areas.

22. The process of claim 21, further comprising:
correcting an image detected by the first fluorescence spectrum after irradiation with the first wavelength, wherein the image is corrected to account for:
the background spectrum detected by the first fluorescence spectrum after irradiation with the first wavelength, wherein the labeled nucleic acid molecules were not disposed on the imaging substrate,
a non-uniformity in an imaging sensor and a spatial distribution of first wavelength;
measuring an intensity of the first fluorescence spectrum detected from single labeled nucleic acid molecules in the image;
producing a calibration between the intensity of the first fluorescence spectrum and the size of a nucleic acid molecule with a reference sample comprising single sizes of reference nucleic acid molecules;
modeling, with a selected function in a model, a dependence of a coefficient of variation of the intensity of the first fluorescence spectrum detected on nucleic acid molecule size;
including, as an input to the model, a measured size of the labeled nucleic acid molecules; and
determining, from the model, an uncertainty of the size of the single nucleic acid molecules of the labeled nucleic acid molecules.

23. The process of claim 1, wherein the nucleic acid molecules have an unknown concentration.

24. The process of claim 1, wherein imaging includes additional spectra that are distinct from the first and second spectra for measurement of additional properties.

25. The process of claim 24, wherein the additional properties are indicated by an imaging target that comprises a fluorescent molecule.

26. The process of claim 24, wherein the additional properties are the association of particular binding proteins or specific mutations with single labeled nucleic acid molecules.

* * * * *